US00PP09023P

United States Patent [19]

Hoff

[11] Patent Number: Plant 9,023

[45] Date of Patent: Dec. 27, 1994

[54] VARIETY OF LILIUM NAMED MARLÈNE

[75] Inventor: Petrus M. M. Hoff, Steenbergen, Netherlands

[73] Assignee: Hoffgaarde B.V., Steenbergen, Netherlands

[21] Appl. No.: 177,196

[22] Filed: Jan. 4, 1994

[51] Int. Cl.[5] ..... A01H 5/00
[52] U.S. Cl. ..... Plt./87.4
[58] Field of Search ..... Plt. 87.4

*Primary Examiner*—James R. Feyrer
*Attorney, Agent, or Firm*—Webb Ziesenheim Bruening Logsdon Orkin & Hanson

[57] ABSTRACT

A new and distinct cultivar of lily plant named Marlène, particularly characterized by pinkish upper surface and ivory lower surface of the flowers, height of about 110 cm, pedicel of 10–12 cm in length with 4–6 flowers, rather strong, smallish leaves, and capable of producing stems and flowers for cut-flower production.

1 Drawing Sheet

BACKGROUND OF THE INVENTION

The present invention comprises a new and distinct cultivar of lily, botanically known as Lilium asiatic and hereinafter referred to by the cultivar name Marlène.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde, B.V., Franseweg 9, 4651 PV Steenbergen, The Netherlands in 1989. The female and male parents were seedlings originated by Applicant, which were proprietary, and maintained by Applicant for breeding purposes.

The new cultivar was discovered and selected as one flowering plant within the progeny of the stated cross by the inventor on May 25, 1991 in a controlled environment in Steenbergen.

The first act of asexual reproduction of the new cultivar was accomplished by the invention when scales were taken from the initial selection on Oct. 30, 1991 in a controlled environment in Steenbergen.

Horticultural examination of selected units initiated Apr. 1, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice.

The following traits have been repeatedly observed and are determined to be basic characteristics of the new cultivar which in combination distinguish this lily as a new and distinct cultivar.

1) Flower color having an interesting white-blushed-with-red at the tips, with tepals having an essentially white ground color centrally, with soft but progressively more intensive red blush with progressive proximity toward apex of each tepal, and with white bottom surfaces.

2) About 110 cm in height.
3) Pedicel 10–12 cm in length with 4–6 flowers.
4) Rather thick and stiff, smallish leaves.

The accompanying color photographic drawing shows typically flower characteristics of the new cultivar, with colors being as true as possible with illustrations of this type.

In the following description, color references are made to the Royal Horticultural Society Colour Chart. The color values were determined at Steenbergen on Apr. 1, 1992.

THE PLANT

Classification:
*Botanic.*—Lilium asiatic.
*Commercial.*—Hybrid asiatic lily for cut flower production.
Form: Single upright stem from each bulb.
Height: About 110 cm.
Growth habit: Upright, erect, strong and vigorous.
Color: Yellow-green Group 144A.
Stem:
*Diameter.*—1 cm average.
*Form.*—Rounded.
Foilage:
*Quantity.*—125–140 leaves.
*Size of leaf.*—About 10 cm long, 1 cm wide up to about 15 cm long, 1.8 cm wide.
*Shape of leaf.*—Narrow oblong.
*Texture of leaf.*—Smooth.
*Color.*—Green Group 137A.
Bulbs:
*Size.*—12–14 cm in circumference.
*Color.*—White.

THE BUD

Form: Oblong, (acute UPOV Type IV).
Size: 10 cm in length.
Color: Red Group 49B or 49C.

THE FLOWER

Blooming habit: 100 days after planting.
Size: 18 cm in diameter.
Borne: Umbellate, single.
Shape: (Narrow acute UPOV Type VIII).
Tepalage:
*Number of tepals.*—6.

*Arrangement.*—Hexagonal, inner tepals about 4–6 mm apart at their bases.

*Size.*—Inner tepals 11 cm long, 3–4 cm wide; Outer tepals 11 cm long, 2–3 cm wide.

*Color.*—Inner and outer tepals. Upper surface: Red Group 49A at apex, Red Group 49B in the middle, White Group 155A at the base. Lower surface: White Group 155A.

*Reflexing.*—None.

*Spotting.*—Few, approximately 1 mm diameter.

Pedicel.

*Length.*—10 cm.

*Color.*—Green.

*Form.*—Upright.

Nectaries:

*Size.*—2 cm long.

*Color.*—Green.

Texture: Smooth.

Disease resistance: No unusual disease problems have been observed.

Fragrance: None.

Lasting quality: 14 days in water after cutting.

REPRODUCTIVE ORGANS

Stamens:

*Number.*—6.

*Length.*—8 cm.

*Anthers-color.*—Reddish brown.

*Pollen-color.*—Greyed-orange Group 171B.

*Filaments-color.*—Pinkish-white.

Pistils: One, long.

*Color.*—Greyed-orange Group 171B.

Stigma.

*Color.*—Brown.

Ovaries:

*Color.*—Green.

I claim:

1. A new and distinct variety of lily plant substantially as shown and described.

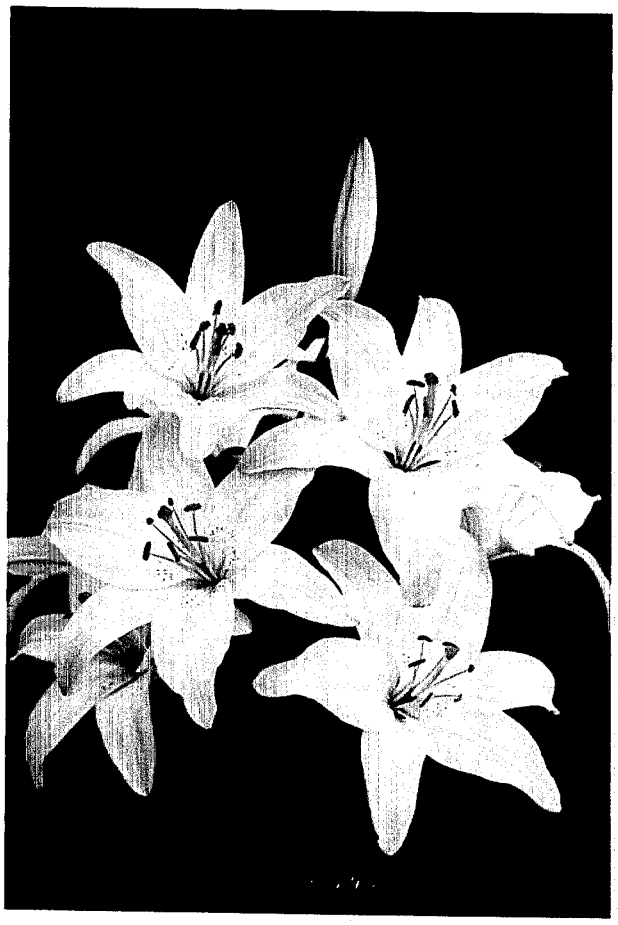

* * * * *